United States Patent
Carnes et al.

(10) Patent No.: US 11,491,028 B2
(45) Date of Patent: Nov. 8, 2022

(54) INSERTION INSTRUMENT FOR EXPANDABLE SPINAL IMPLANTS

(71) Applicant: K2M, Inc., Leesburg, VA (US)

(72) Inventors: Megan Carnes, Leesburg, VA (US); John Donohoe, Morrisville, NC (US); Scott Jones, Mcmurray, PA (US)

(73) Assignee: K2M, Inc., Leesburg, VA (US)

( * ) Notice: Subject to any disclaimer, the term of this patent is extended or adjusted under 35 U.S.C. 154(b) by 116 days.

(21) Appl. No.: 17/026,730

(22) Filed: Sep. 21, 2020

(65) Prior Publication Data

US 2021/0068982 A1  Mar. 11, 2021

Related U.S. Application Data

(60) Division of application No. 16/229,766, filed on Dec. 21, 2018, now Pat. No. 10,786,369, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/447* (2013.01); *A61F 2/4455* (2013.01); *A61F 2/4425* (2013.01);
(Continued)

(58) Field of Classification Search
CPC .......... A61F 2/4425; A61F 2/447; A61F 2/46; A61F 2/4603; A61F 2/4611;
(Continued)

(56) References Cited

U.S. PATENT DOCUMENTS 5,554,191 A   9/1996 Lahille et al.
5,665,122 A   9/1997 Kambin
(Continued)

FOREIGN PATENT DOCUMENTS

FR      2 717 068 A1   9/1995
WO      2014145766 A1  9/2014
(Continued)

OTHER PUBLICATIONS

Australian Search Report for Application No. 2015330678, dated Jul. 5, 2019, p. 1.
(Continued)

*Primary Examiner* — Kevin T Truong
*Assistant Examiner* — Tracy L Kamikawa
(74) *Attorney, Agent, or Firm* — Lerner, David, Littenberg, Krumholz & Mentlik, LLP

(57) ABSTRACT

An insertion instrument for expandable spinal implants includes an elongate member, a shuttle, and a worm gear. The elongate member includes a handle portion of a proximal end and an end effector on a distal end, wherein the end effector is configured to be releasably engaged to an expandable spinal implant. The shuttle is slidably disposed within a cavity defined within the end effector and includes a wedged shaped distal end configured to engage an expandable spinal implant. The worm gear is rotatably disposed within the cavity defined in the end effector and is in mechanical communication with the shuttle, such that rotation of the worm gear effectuates movement of the shuttle. Distal movement of the shuttle effectuates articulation of an expandable spinal implant. A method of performing surgery is also disclosed.

19 Claims, 13 Drawing Sheets

Related U.S. Application Data continuation of application No. 16/071,292, filed on Jun. 25, 2018, now Pat. No. 10,159,584, which is a division of application No. 15/054,452, filed on Feb. 26, 2016, now Pat. No. 10,004,608.

(52) U.S. Cl.
CPC ..... *A61F 2/4637* (2013.01); *A61F 2002/3052* (2013.01); *A61F 2002/30405* (2013.01); *A61F 2002/30471* (2013.01); *A61F 2002/30507* (2013.01); *A61F 2002/30515* (2013.01); *A61F 2002/30538* (2013.01); *A61F 2002/30556* (2013.01); *A61F 2002/30571* (2013.01); *A61F 2002/30593* (2013.01); *A61F 2002/30787* (2013.01); *A61F 2002/30904* (2013.01); *A61F 2002/4615* (2013.01); *A61F 2002/4627* (2013.01); *A61F 2002/4629* (2013.01)

(58) Field of Classification Search
CPC ............... A61F 2/4637; A61F 2/4455; A61F 2002/443; A61F 2002/4475; A61F 2002/448; A61F 2002/4615; A61F 2002/4623; A61F 2002/4625; A61F 2002/4627; A61F 2002/4629; A61F 2002/4638; A61F 2002/4642; A61F 2002/30507; A61F 2002/30556; A61F 2002/30593; A61F 2002/30904

See application file for complete search history.

(56) References Cited

U.S. PATENT DOCUMENTS

| | | |
|---|---|---|
| 6,102,950 A | 8/2000 | Vaccaro |
| 6,159,244 A | 12/2000 | Suddaby |
| 6,174,334 B1 | 1/2001 | Suddaby |
| 6,176,882 B1 | 1/2001 | Biedermann et al. |
| 6,190,414 B1 | 2/2001 | Young et al. |
| 6,200,348 B1 | 3/2001 | Biedermann et al. |
| 6,332,895 B1 | 12/2001 | Suddaby |
| 6,395,031 B1 | 5/2002 | Foley et al. |
| 6,409,766 B1 | 6/2002 | Brett |
| 6,436,140 B1 | 8/2002 | Liu et al. |
| 6,443,989 B1 | 9/2002 | Jackson |
| 6,454,807 B1 | 9/2002 | Jackson |
| 6,491,724 B1 | 12/2002 | Ferree |
| 6,576,016 B1 | 6/2003 | Hochshuler et al. |
| 6,641,614 B1 | 11/2003 | Wagner et al. |
| 6,685,742 B1 | 2/2004 | Jackson |
| 6,709,458 B2 | 3/2004 | Michelson |
| 6,716,247 B2 | 4/2004 | Michelson |
| 6,773,460 B2 | 8/2004 | Jackson |
| 6,808,537 B2 | 10/2004 | Michelson |
| 6,814,756 B1 | 11/2004 | Michelson |
| 6,835,206 B2 | 12/2004 | Jackson |
| 6,852,129 B2 | 2/2005 | Gerbec et al. |
| 6,863,673 B2 | 3/2005 | Gerbec et al. |
| 6,962,606 B2 | 11/2005 | Michelson |
| 6,972,035 B2 | 12/2005 | Michelson |
| 7,008,453 B1 | 3/2006 | Michelson |
| 7,044,971 B2 | 5/2006 | Suddaby |
| 7,118,579 B2 | 10/2006 | Michelson |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,588,573 B2 | 9/2009 | Berry |
| 7,618,458 B2 | 11/2009 | Biedermann et al. |
| 7,655,027 B2 | 2/2010 | Michelson |
| 7,678,148 B2 | 3/2010 | Peterman |
| 7,691,147 B2 | 4/2010 | Gutlin et al. |
| 7,708,779 B2 | 5/2010 | Edie et al. |
| 7,722,674 B1 | 5/2010 | Grotz |
| 7,731,751 B2 | 6/2010 | Butler et al. |
| 7,771,473 B2 | 8/2010 | Thramann |
| 7,776,091 B2 | 8/2010 | Mastrorio et al. |
| 7,794,501 B2 | 9/2010 | Edie et al. |
| 7,799,081 B2 | 9/2010 | McKinley |
| 7,828,849 B2 | 11/2010 | Lim |
| 7,850,733 B2 | 12/2010 | Baynham et al. |
| 7,883,542 B2 | 2/2011 | Zipnick |
| 7,909,870 B2 | 3/2011 | Kraus |
| 7,922,729 B2 | 4/2011 | Michelson |
| 7,967,867 B2 | 6/2011 | Barreiro et al. |
| 8,062,366 B2 | 11/2011 | Melkent |
| 8,062,375 B2 | 11/2011 | Glerum et al. |
| 8,075,621 B2 | 12/2011 | Michelson |
| 8,097,034 B2 | 1/2012 | Michelson |
| 8,105,382 B2 | 1/2012 | Olmos et al. |
| 8,110,004 B2 | 2/2012 | Valdevit et al. |
| 8,118,871 B2 | 2/2012 | Gordon et al. |
| 8,123,810 B2 | 2/2012 | Gordon et al. |
| 8,133,232 B2 | 3/2012 | Levy et al. |
| 8,137,405 B2 | 3/2012 | Kostuik et al. |
| 8,147,550 B2 | 4/2012 | Gordon et al. |
| 8,152,851 B2 | 4/2012 | Mueller et al. |
| 8,152,852 B2 | 4/2012 | Biyani |
| 8,172,903 B2 | 5/2012 | Gordon et al. |
| 8,182,537 B2 | 5/2012 | Refai et al. |
| 8,187,331 B2 | 5/2012 | Strohkirch, Jr. et al. |
| 8,192,495 B2 | 6/2012 | Simpson et al. |
| 8,197,546 B2 | 6/2012 | Doubler et al. |
| 8,211,178 B2 | 7/2012 | Melkent et al. |
| 8,221,502 B2 | 7/2012 | Branch, Jr. |
| 8,231,656 B2 | 7/2012 | Lee et al. |
| 8,257,440 B2 | 9/2012 | Gordon et al. |
| 8,257,442 B2 | 9/2012 | Edie et al. |
| 8,273,126 B2 | 9/2012 | Lindner |
| 8,303,663 B2 | 11/2012 | Jimenez et al. |
| 8,308,802 B2 | 11/2012 | Rhoda et al. |
| 8,328,871 B2 | 12/2012 | Capote et al. |
| 8,337,558 B2 | 12/2012 | Lindner |
| 8,337,559 B2 | 12/2012 | Hansell et al. |
| 8,349,014 B2 | 1/2013 | Barreiro et al. |
| 8,353,961 B2 | 1/2013 | Mcclintock et al. |
| 8,366,777 B2 | 2/2013 | Matthis et al. |
| 8,382,842 B2 | 2/2013 | Greenhalgh et al. |
| 8,394,143 B2 | 3/2013 | Grotz et al. |
| 8,398,713 B2 | 3/2013 | Weiman |
| 8,425,608 B2 | 4/2013 | Dewey et al. |
| 8,435,296 B2 | 5/2013 | Kadaba et al. |
| 8,480,738 B2 | 7/2013 | Edie et al. |
| 8,496,706 B2 | 7/2013 | Ragab et al. |
| 8,512,406 B2 | 8/2013 | White et al. |
| 8,518,114 B2 | 8/2013 | Marik |
| 8,628,578 B2 | 1/2014 | Miller et al. |
| 8,663,329 B2 | 3/2014 | Ernst |
| 8,679,183 B2 | 3/2014 | Glerum et al. |
| 8,721,723 B2 | 5/2014 | Hansell et al. |
| 8,795,366 B2 | 8/2014 | Varela |
| 8,845,733 B2 | 9/2014 | O'Neil et al. |
| 8,894,711 B2 | 11/2014 | Varela |
| 9,034,045 B2 | 5/2015 | Davenport et al. |
| 9,198,769 B2 | 12/2015 | Perrow et al. |
| 9,271,846 B2 | 3/2016 | Lim et al. |
| 9,393,130 B2 | 7/2016 | Suddaby et al. |
| 9,572,680 B2 | 2/2017 | Theofilos et al. |
| 9,585,762 B2 | 3/2017 | Suddaby et al. |
| 9,808,352 B2 | 11/2017 | Suddaby et al. |
| 9,839,528 B2 | 12/2017 | Weiman et al. |
| 9,872,777 B2 | 1/2018 | Ganter et al. |
| 2002/0068976 A1 | 6/2002 | Jackson |
| 2002/0128712 A1 | 9/2002 | Michelson |
| 2002/0128713 A1 | 9/2002 | Ferree |
| 2002/0177897 A1 | 11/2002 | Michelson |
| 2004/0059421 A1 | 3/2004 | Glenn et al. |
| 2004/0087947 A1 | 5/2004 | Lim et al. |
| 2004/0249461 A1* | 12/2004 | Ferree .................. A61F 2/2846 623/17.11 |
| 2004/0254643 A1 | 12/2004 | Jackson |
| 2005/0015149 A1 | 1/2005 | Michelson |
| 2005/0125061 A1 | 6/2005 | Zucherman et al. |
| 2006/0030943 A1 | 2/2006 | Peterman |

(56) References Cited

U.S. PATENT DOCUMENTS

| | | |
|---|---|---|
| 2006/0122701 A1 | 6/2006 | Kiester |
| 2006/0167547 A1 | 7/2006 | Suddaby |
| 2006/0195095 A1 | 8/2006 | Mueller et al. |
| 2006/0200244 A1 | 9/2006 | Assaker |
| 2007/0016221 A1 | 1/2007 | Beyersdorff et al. |
| 2007/0270964 A1 | 11/2007 | Strohkirch et al. |
| 2008/0004705 A1 | 1/2008 | Rogeau et al. |
| 2008/0045968 A1 | 2/2008 | Yu et al. |
| 2009/0099568 A1 | 4/2009 | Lowry et al. |
| 2009/0204215 A1 | 8/2009 | McClintock et al. |
| 2009/0281625 A1 | 11/2009 | Enayati |
| 2010/0057208 A1 | 3/2010 | Dryer et al. |
| 2010/0094424 A1 | 4/2010 | Woodburn et al. |
| 2010/0145455 A1 | 6/2010 | Simpson et al. |
| 2010/0262247 A1 | 10/2010 | Arnin |
| 2010/0280616 A1 | 11/2010 | Frasier |
| 2010/0286777 A1* | 11/2010 | Errico .................. A61F 2/4455 606/279 |
| 2010/0324687 A1 | 12/2010 | Melkent et al. |
| 2011/0172774 A1 | 7/2011 | Varela |
| 2011/0319997 A1 | 12/2011 | Glerum et al. |
| 2012/0029636 A1 | 2/2012 | Ragab et al. |
| 2012/0029637 A1 | 2/2012 | Ragab et al. |
| 2012/0185045 A1 | 7/2012 | Morris et al. |
| 2012/0185049 A1 | 7/2012 | Varela |
| 2012/0226357 A1 | 9/2012 | Varela |
| 2012/0310350 A1 | 12/2012 | Farris et al. |
| 2013/0116791 A1 | 5/2013 | Theofilos |
| 2013/0158663 A1 | 6/2013 | Miller |
| 2013/0158664 A1 | 6/2013 | Palmatier et al. |
| 2013/0197642 A1 | 8/2013 | Ernst |
| 2013/0211526 A1 | 8/2013 | Alheidt et al. |
| 2014/0188225 A1 | 7/2014 | Dmuschewsky |
| 2014/0214166 A1 | 7/2014 | Theofilos |
| 2014/0243982 A1 | 8/2014 | Miller |
| 2014/0277479 A1 | 9/2014 | Raymond et al. |
| 2014/0277502 A1 | 9/2014 | Schiffman et al. |
| 2014/0309741 A1* | 10/2014 | Ganter .................. A61F 2/442 623/17.16 |
| 2014/0343678 A1* | 11/2014 | Suddaby ............... A61F 2/4611 623/17.16 |
| 2015/0012098 A1 | 1/2015 | Eastlack et al. |
| 2015/0057755 A1 | 2/2015 | Suddaby et al. |
| 2015/0250609 A1 | 9/2015 | McLean et al. |
| 2016/0022433 A1 | 1/2016 | Davenport |
| 2016/0100951 A1 | 4/2016 | Suddaby et al. |
| 2018/0368987 A9* | 12/2018 | Davis .................. A61F 2/30771 |

FOREIGN PATENT DOCUMENTS

| | | |
|---|---|---|
| WO | 2015063721 A1 | 5/2015 |
| WO | 2016057940 A1 | 4/2016 |

OTHER PUBLICATIONS

European Search Report dated Aug. 7, 2017 issued in corresponding European Application No. 7157602.8-1501.
European Search Report dated Dec. 12, 2016, issued in EP Application No. 14801054.
International Preliminary Report on Patentability dated Nov. 24, 2015, issued in PCT/US2014/038726.
International Search Report dated Sep. 30, 2014 issued in PCT/US2014/038726.
International Search Report for PCT/US2015/054969 dated Jan. 8, 2016.

* cited by examiner

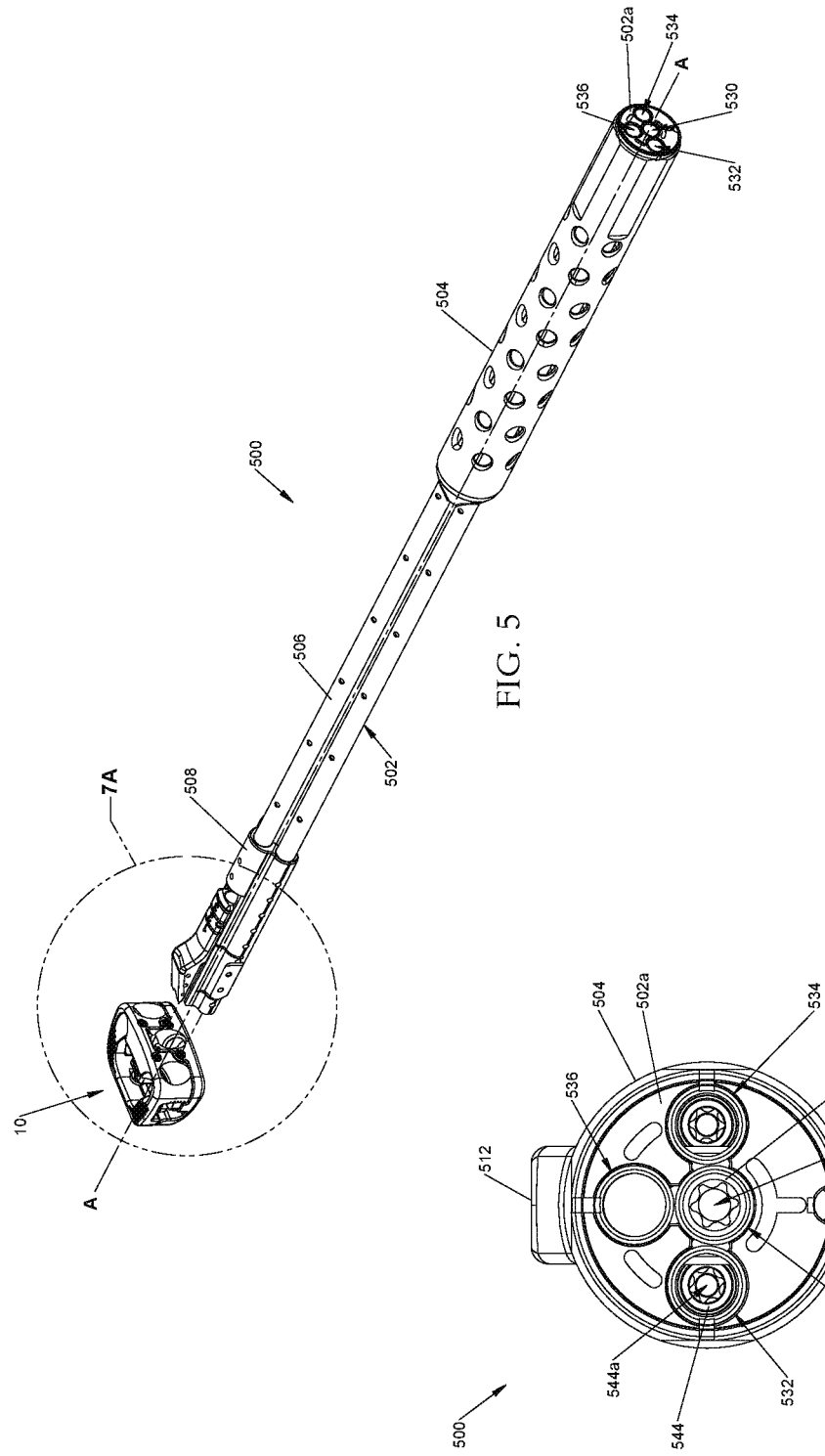

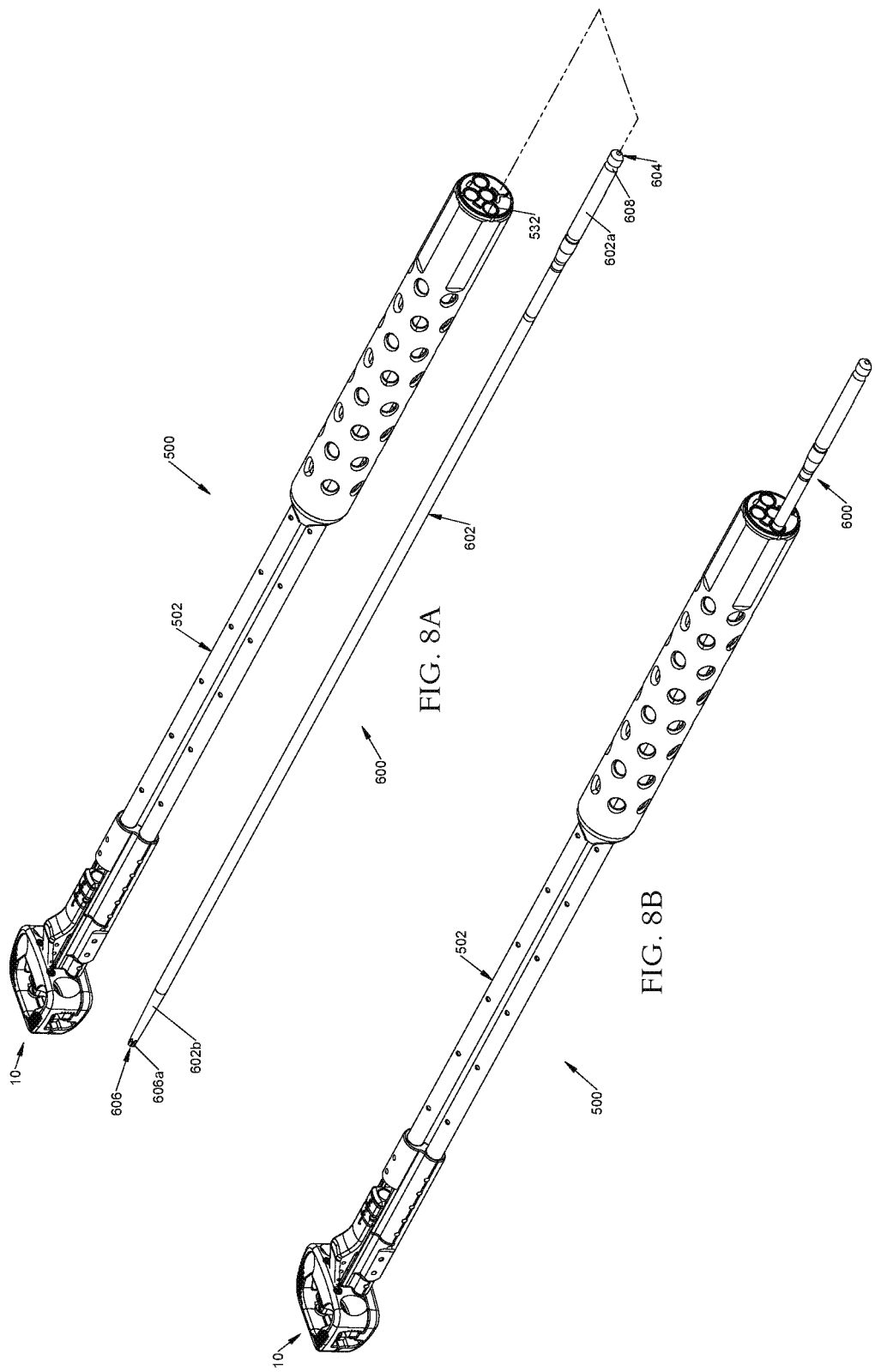

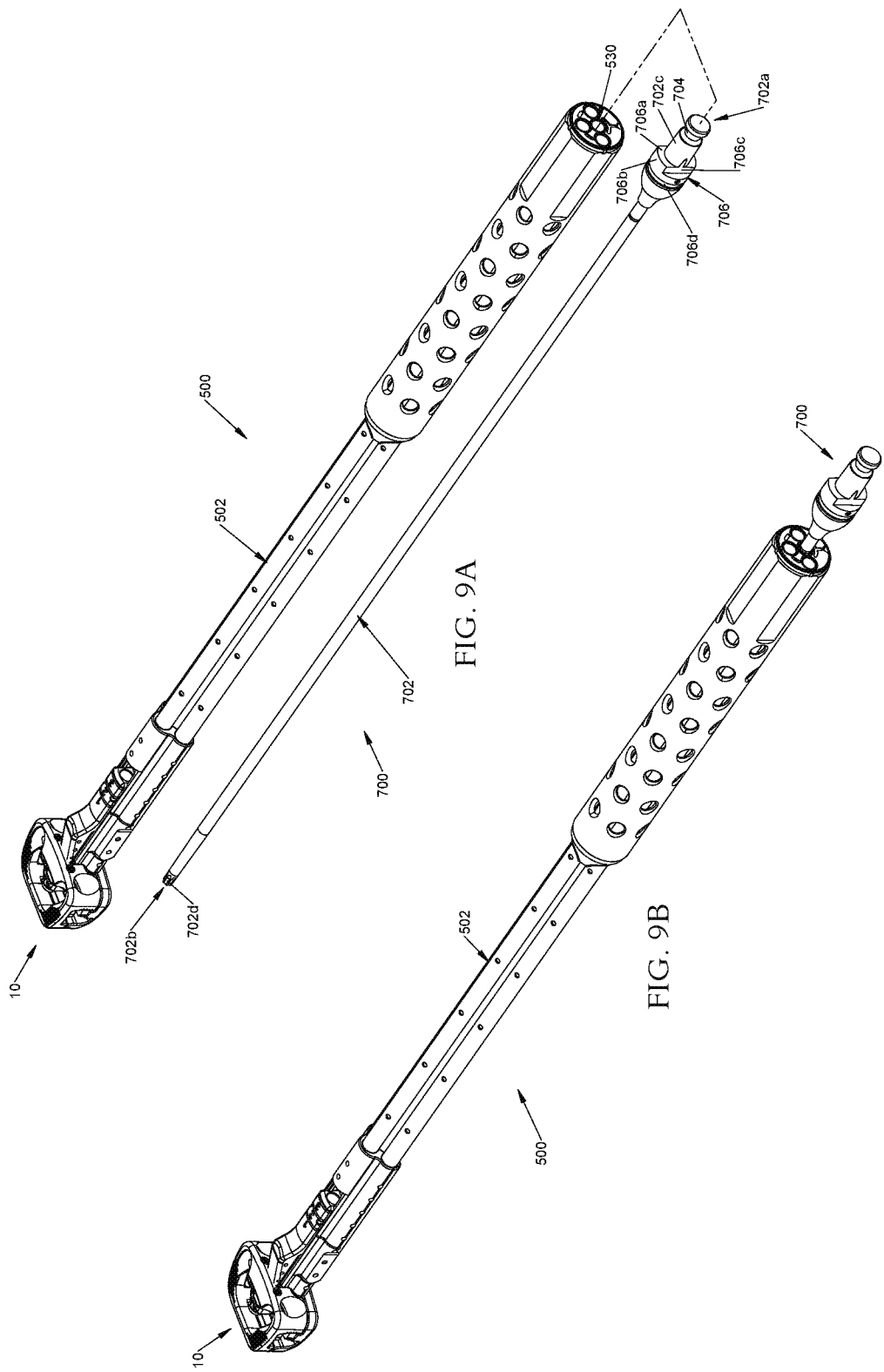

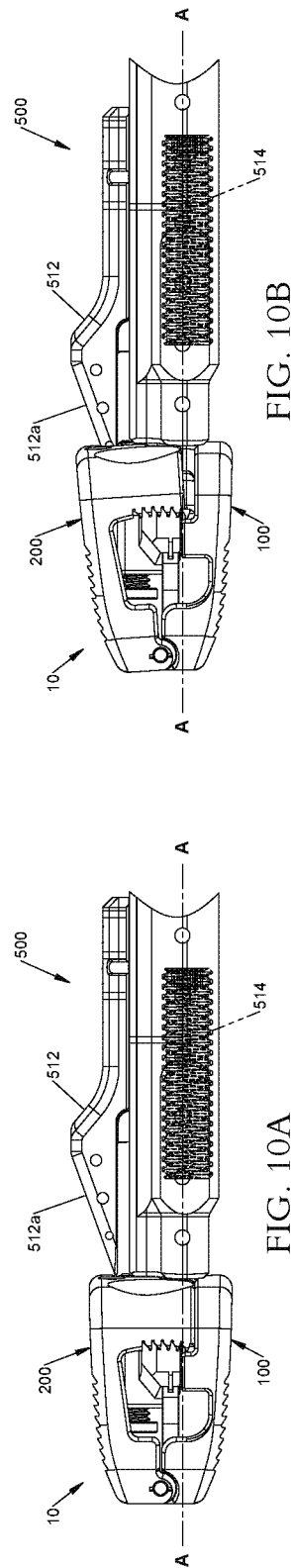
FIG. 10A
FIG. 10B
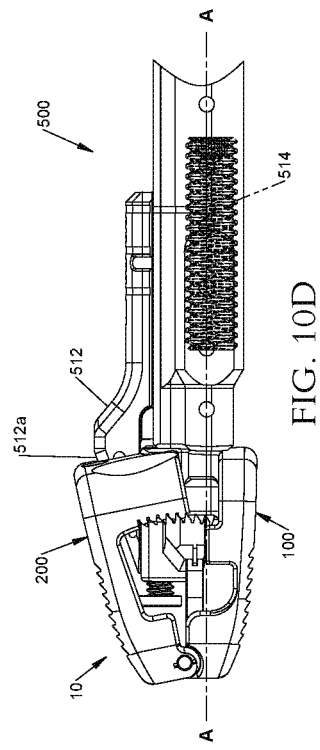
FIG. 10C
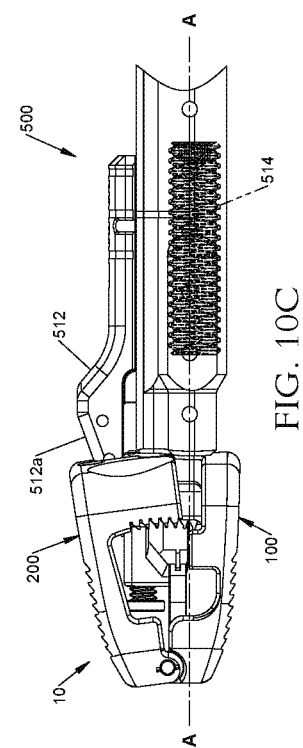
FIG. 10D

INSERTION INSTRUMENT FOR EXPANDABLE SPINAL IMPLANTS

CROSS-REFERENCE TO RELATED APPLICATION

This application is a divisional application of U.S. patent application Ser. No. 16/229,766, filed Dec. 21, 2018, which is a continuation of U.S. patent application Ser. No. 16/017,292, filed Jun. 25, 2018, which is a divisional application of U.S. patent application Ser. No. 15/054,452, filed on Feb. 26, 2016, the disclosures of which are incorporated herein by reference.

BACKGROUND

Technical Field

The present disclosure relates generally to devices and methods for treating spinal conditions, and in particular, to insertion instruments configured for positioning expandable spinal implants within an intervertebral space.

Background of the Disclosure

After a partial or complete discectomy, the normally occupied space between adjacent vertebral bodies may collapse and/or become misaligned due to the absence of all or a part of the intervertebral disc. In these situations, a physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth has occurred.

Additionally, achieving the desired lordosis can be difficult given the limitations of typical prosthetic implants once they are implanted.

To solve these issues, implants capable of providing a desired amount of lordosis, allowing for bone growth between adjacent vertebrae, maintaining the space between adjacent vertebrae during bone ingrowth, and resisting dislocation from its implantation site have been developed. However, effectively implanting such devices can be difficult. Therefore, a need exists for insertion instruments capable of inserting an expandable spinal implant between adjacent vertebrae, manipulating the spinal implant to provide the desired amount of lordosis, and locking the implant in the position providing the desired amount of lordosis.

SUMMARY

In accordance with the present disclosure, an insertion instrument for expandable spinal implants including an elongate member, a shuttle, and a worm gear is provided. The elongate member includes a handle portion on a proximal end thereof and an end effector on a distal end thereof. The end effector is configured to be releasably engaged to an expandable spinal implant. The shuttle is slidably disposed within a cavity defined in the end effector. The shuttle includes a wedge shaped distal end configured to engage an expandable spinal implant. The worm gear is rotatably disposed within the cavity defined in the end effector and is in mechanical communication with the shuttle such that rotation of the worm gear effectuates movement of the shuttle. Distal movement of the shuttle effectuates articulation of an expandable spinal implant.

In aspects, the insertion instrument may include a first tool capable of coupling the end effector to an expandable spinal implant.

In other aspects, the insertion instrument may include a second tool capable of engaging the worm gear and effectuating rotation thereof.

In certain aspects, the elongate member may further include a plurality of throughholes defined therethrough.

In some aspects, the plurality of throughholes may include a first throughhole configured to receive the second tool therethrough.

In certain aspects, the plurality of throughholes may include a second and a third throughhole configured to receive the first tool therethrough to enable the end effector to be releasably secured to an expandable spinal implant.

In other aspects, the plurality of throughholes may include a fourth throughhole configured to receive the first tool therethrough to lock a position of a lower body in relation to a position of an upper body of an expandable spinal implant.

In aspects, the insertion instrument may include a plurality of screws, wherein each of the second and third throughholes is configured to receive a respective screw of the plurality of screws therein, the plurality of screws being configured to releasably couple the end effector to an expandable spinal implant.

In certain aspects, the cavity defined in the end effector may include a pair of opposed rails disposed on side surfaces thereof. The pair of opposed rails may be configured to slidably engage a corresponding pair of opposed slots defined within side surfaces of the shuttle.

An expandable spinal implant is also provided in accordance with the present disclosure and includes an upper body, a lower body, a ratchet mechanism, a biasing element, and a plurality of bone screws. The upper and lower bodies are affixed at a first end and are capable of movement relative to each other. The upper and lower bodies are dimensioned to be installed between two vertebral bodies and the outer surfaces of each are adapted to engage a corresponding end plate of the two vertebral bodies. Screw holes are defined through the outer surface and an adjacent side surface of the upper body and through the outer surface and an adjacent side surface of the lower body. The screw holes are oriented toward a respective adjacent one of the two vertebral bodies at an oblique angle. The ratchet mechanism is slidably disposed on one of the upper and lower bodies and is capable of engaging the opposite one of the upper and lower bodies. The biasing element is capable of biasing the ratchet mechanism in a direction such that the upper and lower bodies are capable of articulating relative to each other in a first direction, but not in a second direction. Each bone screw of the plurality of bone screws is insertable through a corresponding screw hole of the upper body and the lower body and are capable of being attached to bone.

A method of performing surgery provided in accordance with the present disclosure includes releasably securing an insertion instrument to an expandable spinal implant, the insertion instrument including an elongate member, a shuttle, and a worm gear. The elongate member includes a handle portion on a proximal end thereof and an end effector on a distal end thereof. The end effector is configured to be releasably engaged to an expandable spinal implant. The shuttle is slidably disposed within a cavity in the end effector and includes a wedge shaped distal end configured to engage an expandable spinal implant. The worm gear is rotatable disposed within the cavity defined in the end effector. The worm gear is in mechanical communication with the shuttle such that rotation of the worm gear effectuates movement of the shuttle. Distal movement of the shuttle effectuates articulation of an expandable spinal implant.

The method also includes positioning an upper body and a lower body of the expandable spinal implant in a first, approximated position relative to each other, inserting the expandable spinal implant into a prepared intervertebral space, and rotating the worm gear to effectuate distal movement of the shuttle such that the shuttle causes the lower body of the expandable spinal implant to articulate relative to the upper body, thereby effectuating a desired lordosis of a spine of a patient.

In aspects, the method may include inserting a plurality of bone screws within a plurality of screw holes defined in each of the upper and lower bodies of the expandable spinal implant and into respective vertebral bodies.

In some aspects, the method may include locking the upper and lower bodies of the expandable spinal implant relative to each other.

In other aspects, the method may include removing the insertion instrument from the expandable spinal implant.

In certain aspects, releasably securing the insertion instrument to the expandable spinal implant may include engaging a first tool to a plurality of screws disposed within the end effector of the insertion instrument. The plurality of screws may be configured to threadably engage a corresponding plurality of threaded holes defined in the upper body of the expandable spinal implant.

In some aspects, rotating the worm gear may include engaging a second tool to the worm gear such that rotation of the second tool effectuates rotation of the worm gear.

In aspects, rotating the worm gear may include advancing the second tool through a first throughhole defined through the elongate member of the insertion instrument such that the second tool engages the worm gear.

In other aspects, releasably securing the insertion instrument to the expandable spinal implant includes advancing the first tool through a second and a third throughhole defined through the elongate member of the insertion instrument such that the first tool engages each screw of the plurality of screws.

In certain aspects, locking the upper and lower bodies of the expandable spinal implant includes engaging a first tool to a ratchet screw rotatably disposed on the upper body. The ratchet screw may threadably engage a ratchet mechanism slidably disposed on the upper body, wherein rotation of the ratchet screw causes a plurality of teeth disposed on the ratchet mechanism to engage a corresponding plurality of teeth disposed on the lower body of the expandable spinal implant thereby locking the upper body relative to the lower body.

In some aspects, locking the upper and lower bodies of the expandable spinal implant includes advancing the first tool within a fourth throughhole defined through the elongate member of the insertion instrument.

BRIEF DESCRIPTION OF THE DRAWINGS

The above and other aspects, features, and advantages of the present disclosure will become more apparent in light of the following detailed description when taken in conjunction with the accompanying drawings in which:

FIG. 5 is a rear, perspective view, of an insertion instrument and the expandable spinal implant of FIG. 1 provided in accordance with the present disclosure;

FIG. 6 is a rear view of the insertion instrument of FIG. 5;

FIG. 8A is a rear, perspective view, of the insertion instrument of FIG. 5, shown with a first tool;

FIG. 8B is a rear, perspective view, of the insertion instrument of FIG. 5, shown with the first tool of FIG. 8A advanced within a second throughhole defined therein;

FIG. 9A is a rear, perspective view, of the insertion instrument of FIG. 5, shown with a second tool;

FIG. 9B is a rear, perspective view, of the insertion instrument of FIG. 5, shown with the second tool of FIG. 9A advanced within a first throughhole defined therein;

FIG. 10A is a side view of the insertion instrument of FIG. 5 coupled to the expandable spinal implant of FIG. 1;

FIG. 10B is a side view of a shuttle of the insertion instrument of FIG. 5 partially disposed within the expandable spinal implant of FIG. 1;

FIG. 10C is a side view of the shuttle of the insertion instrument of FIG. 5, shown as being further advanced within the expandable spinal implant of FIG. 1;

FIG. 10D is a side view of the shuttle of the insertion instrument of FIG. 5, shown as being advanced even further within the expandable spinal implant of FIG. 1;

DETAILED DESCRIPTION OF THE EMBODIMENTS

Figure 1:
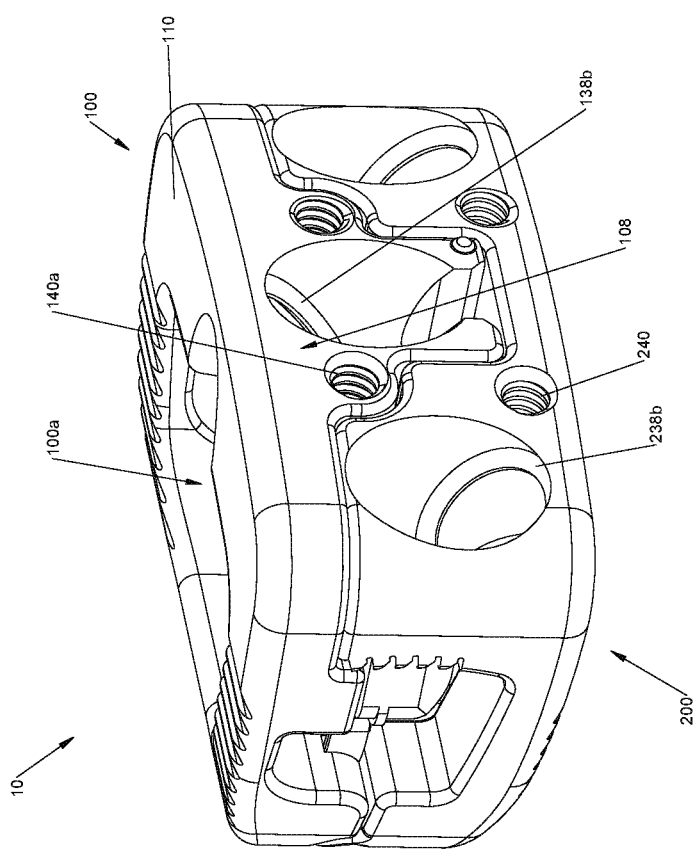
FIG. 1 is a rear, perspective view, of an expandable spinal implant provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 2:
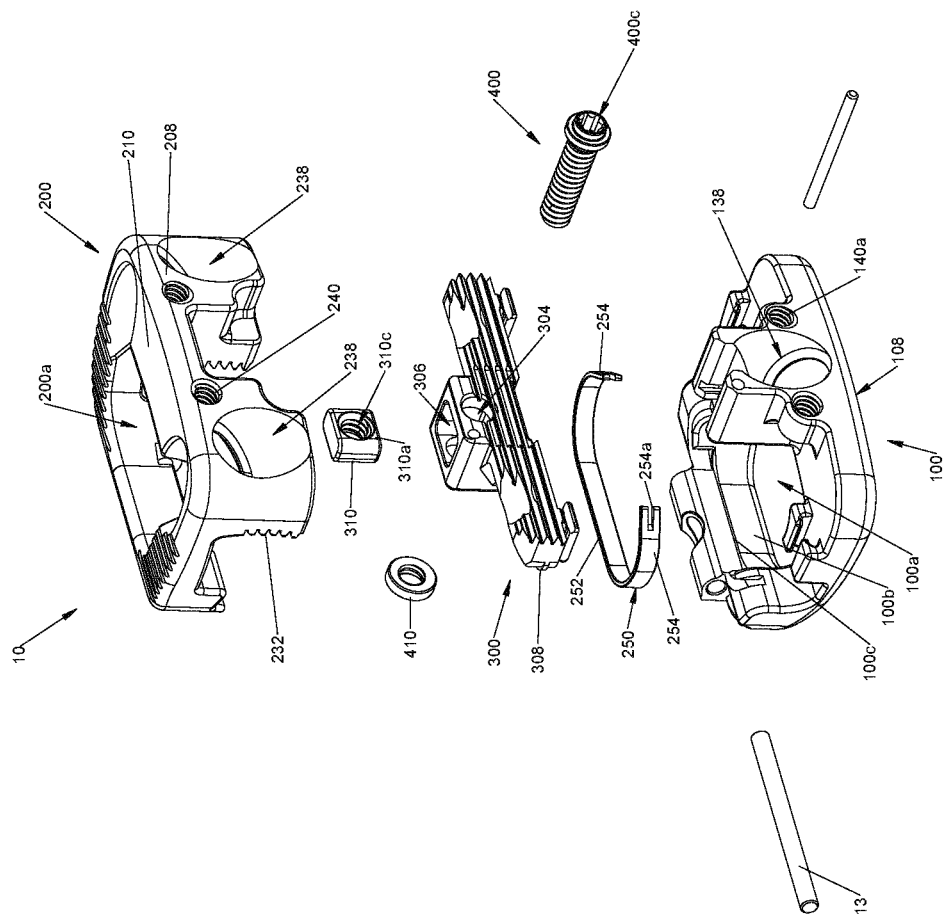
FIG. 2 is an exploded view, with parts separated, of the expandable spinal implant of FIG. 1.
Figure 3:
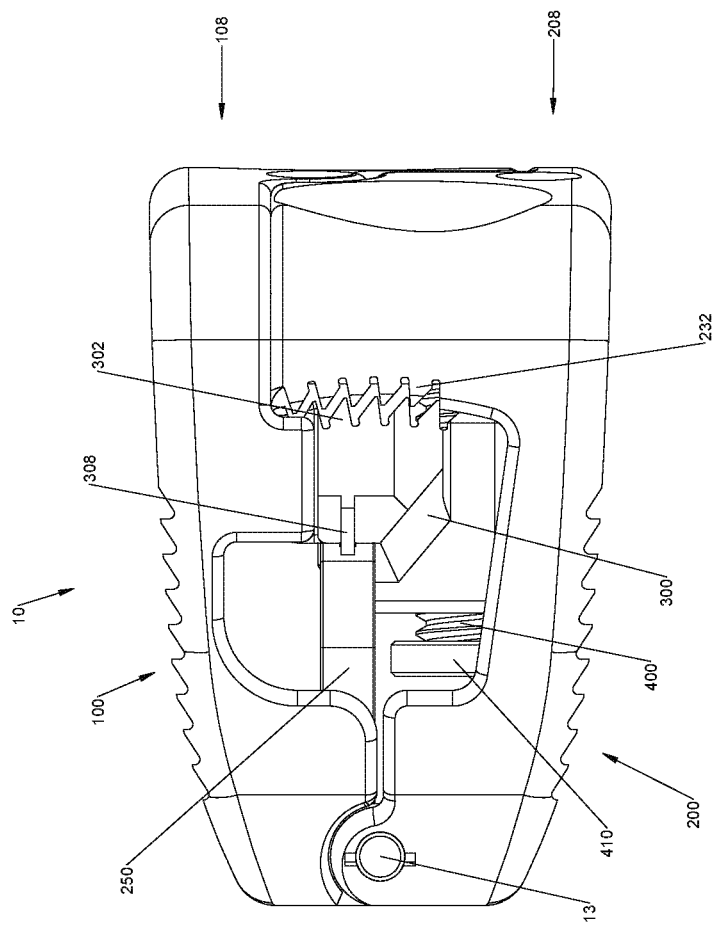
FIG. 3 is a side view of the expandable spinal implant of FIG. 1.

Referring now to the drawings, FIGS. 1-3 illustrate an expandable spinal implant 10 provided in accordance with the present disclosure that is capable being used with an insertion instrument 500 (FIG. 5), as will be described in further detail hereinbelow. Expandable spinal implant 10 includes an upper body 100, a lower body 200, leaf spring 250, and a ratchet 300 including a shuttle nut 310, ratchet screw 400, and stop washer 410 (FIG. 2). Upper and lower bodies 100, 200 cooperate to define a two part expandable spinal implant configured for positioning between adjacent vertebral bodies. Hinge pin 13 rotatably retains upper and lower bodies 100, 200 in order to permit upper and lower bodies 100, 200, respectively, to rotate or articulate thereabout, thereby effectuating lordosis of the spine. Ratchet 300, leaf spring 250, shuttle nut 310, ratchet screw 400, and stop washer 410 cooperate to provide a locking mechanism to lock upper and lower bodies 100, 200 in an articulated position relative to each other, thereby maintaining the desired lordosis of the spine. In this manner, rotation of ratchet screw 400 causes shuttle nut 310 translate in a proximal or distal direction (i.e., towards or away from trailing end 108) thereby causing ratchet 300 to translate between a locked and an unlocked position.

A first opening 100a is defined through a top surface 110 of upper body 100 and a second opening 200a is defined through a bottom surface of lower body 200. First and second openings 100a, 200a define a cavity therebetween and include a shape generally complimentary to the shape of upper and lower bodies 100, 200, although it is contemplated that first and second openings 100a, 200a may include any suitable shape, such as square, oval, circular, or the like.

Ratchet 300 is slidably disposed on upper body 100 and includes a plurality of teeth 302 disposed thereon configured to engage a corresponding plurality of teeth 232 disposed on lower body 200 as ratchet 300 is advanced from an unlocked position to a locked position. Once engaged, teeth 302 and 232 maintain lower body 200 and upper body 100 in a selected position relative to each other. A through-bore 304 is defined through ratchet 300 and is configured to slidably receive ratchet screw 400 therein. Stop washer 410 is fixedly secured to a distal end of ratchet screw 400, such that ratchet 300 may not be advanced distally such that ratchet 300 becomes disengaged from ratchet screw 400. Stop washer 410 may be retained on ratchet screw 400 by any means known in the art, such as bonding, welding, etc.

Ratchet screw 400 is rotatably disposed within upper body 100 and includes a tool engaging recess 400c defined therein configured to engage distal tip 606a of first tool 600 (FIG. 8A). In this manner, rotation of first tool 600 effectuates rotation of ratchet screw 400, thereby effectuating movement of shuttle nut 310, as will be described in further detail hereinbelow.

Leaf spring 250 includes a generally open trapezoidal profile and is configured and/or dimensioned to be interposed between a proximal facing interior surface 100b of first opening 100a and shuttle 300. In this manner, leaf spring 250 includes a backspan 252 and a pair of proximally extending arms 254. Each arm 254 is oriented in a medial direction, such that arms 254 extend towards one another. A slot 254a is defined on a proximal end of each arm 254 and is configured to engage a ridge 308 defined on a distal end of ratchet 300.

Backspan 252 is configured to be disposed in recess 100c defined in proximal facing interior surface 100b of first opening 100a, and each arm of the pair of proximally extending arms 254 is compressed an initial amount such that when leaf spring 250 is interposed between upper body 100 and ratchet 300, ratchet 300 is biased in a proximal direction.

The open configuration of leaf spring 250 enables a clinician to pack openings 100a, 200a of upper and lower bodies 100, 200, respectively, with bone in-growth material, drugs, or other suitable materials or compounds, as will be described in further detail hereinbelow. In this manner, leaf spring 250 minimally impacts the volume of material that can be packed within openings 100a, 200a. However, it is contemplated that leaf spring 250 may include any suitable profile capable of biasing ratchet 300 in a proximal direction, such as V-shaped, C-shaped, U-shaped, wave, etc. or leaf spring 250 may be any suitable biasing element or elements, such as a coil spring, a plurality of coils springs, Bellville washer(s) of any suitable profile, torsion, or the like. Alternatively, it is contemplated that one or more coil springs, Bellville washers, or other suitable biasing elements may be disposed within cavity 306 of ratchet 300 (further detailed hereinbelow) such that the biasing element is interposed between shuttle nut 310 and ratchet 300 thereby biasing ratchet 300 in a proximal direction. In embodiments, the biasing element may be coaxially disposed around ratchet screw 400.

A cavity 306 is defined through an upper surface 300a of ratchet 300 and is configured and dimensioned to receive shuttle nut 310 therein. Although shown as including a generally square profile, it is contemplated that shuttle nut 310 may include any suitable profile, such as circular, oval, rectangular, or the like. A threaded bore 310c is defined through a proximal face 310a and a distal face (not shown) of shuttle nut 310 and is configured to threadably engage ratchet screw 400. In this manner, threaded bore 310c is coaxially aligned with through-bore 304 of ratchet 300 when shuttle nut is fully nested within cavity 306. Shuttle nut 310 is configured to be translated proximally such that proximal face 310a is drawn into contact with ratchet 300 and urges ratchet 300 towards a locked position (i.e., towards trailing end 108). In this manner, leaf spring 250 biases ratchet 300 such that teeth 302 and 232 engage one another. When placed in a locked position, shuttle nut 310 prevents ratchet 300 from translating in a distal direction (i.e., towards leading end), thereby maintaining engagement between teeth 302 and 232.

Shuttle nut 310 is also configured to be translated distally such that a distal face (not shown) of shuttle nut 310 is drawn into contact with ratchet 300 and causes ratchet 300 to translate to an unlocked position. In this manner, shuttle nut 310 causes ratchet 300 to overcome the biasing force provided by leaf spring 250, thereby causing teeth 302 and 232 to disengage, thereby allowing upper and lower bodies 100, 200 to articulate relative to one another.

As can be appreciated, shuttle nut 310 is configured to be placed in an intermediate position where shuttle nut 310 does not urge ratchet 300 in a distal direction. Rather, shuttle nut 310 is placed in a position where ratchet 300 is permitted to translate in a distal direction, thereby permitting teeth 302 and 232 to cam over one another. In this manner, as teeth 302 and 232 cam over one another, upper and lower bodies 100, 200 articulate relative to one another throughout a plurality of positions defined by positions in which teeth 302 and 232 are engaged.

Figures 7A, 7B:
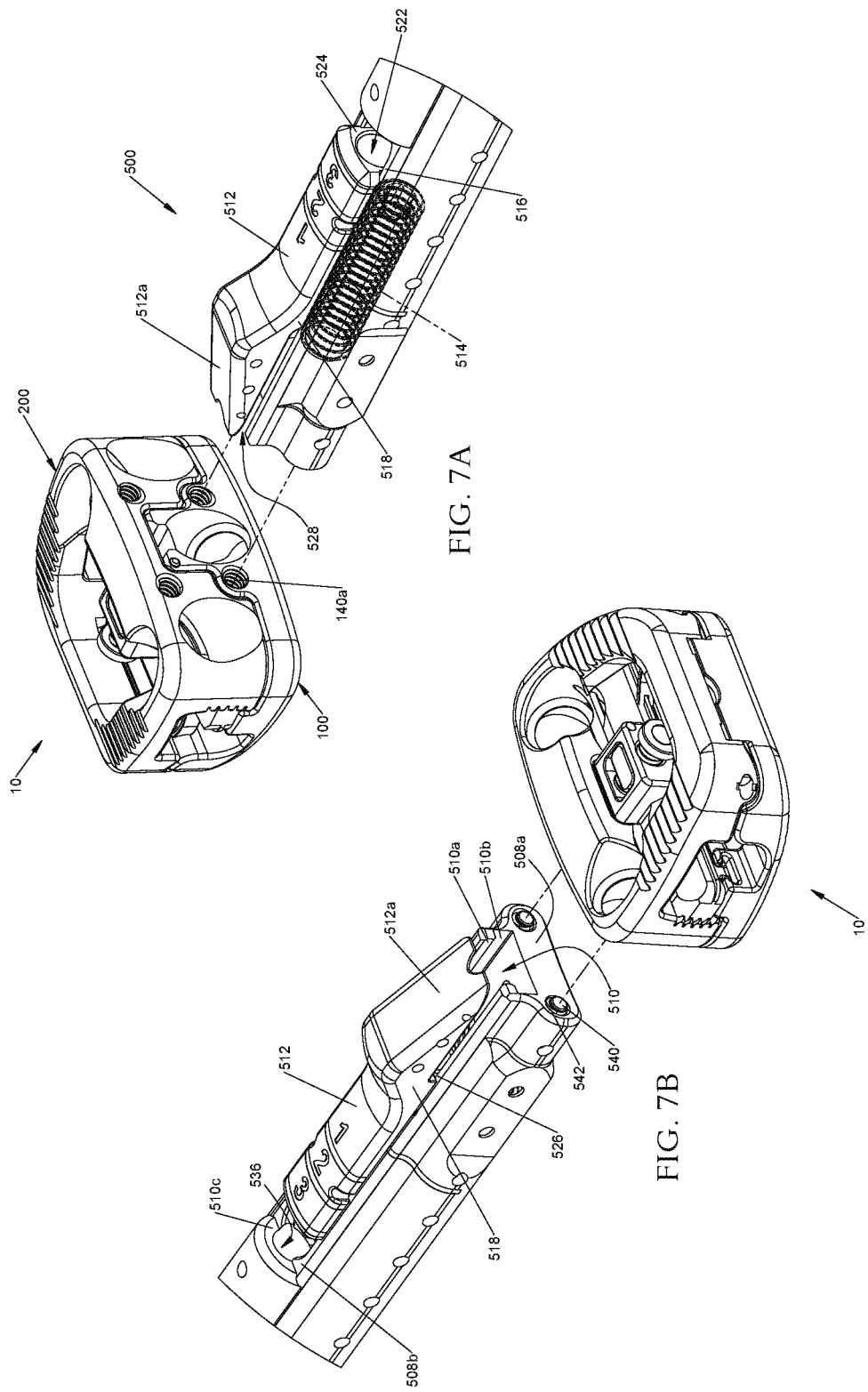
FIG. 7A is an enlarged view of the area of detail indicated in FIG. 5.
FIG. 7B is an front, perspective view, of the enlarged view of FIG. 7A.

A plurality of threaded bores 140a and 240 are defined through a trailing end 108 of upper body and a trailing end 208 of lower body 200, respectively, and are configured to threadably engage screws 540 of insertion instrument 500 (FIG. 7B). In this manner, expandable spinal implant 10 may be releasably engaged to insertion instrument 500 to permit insertion, and manipulation thereof, within the intervertebral space.

Figure 12:
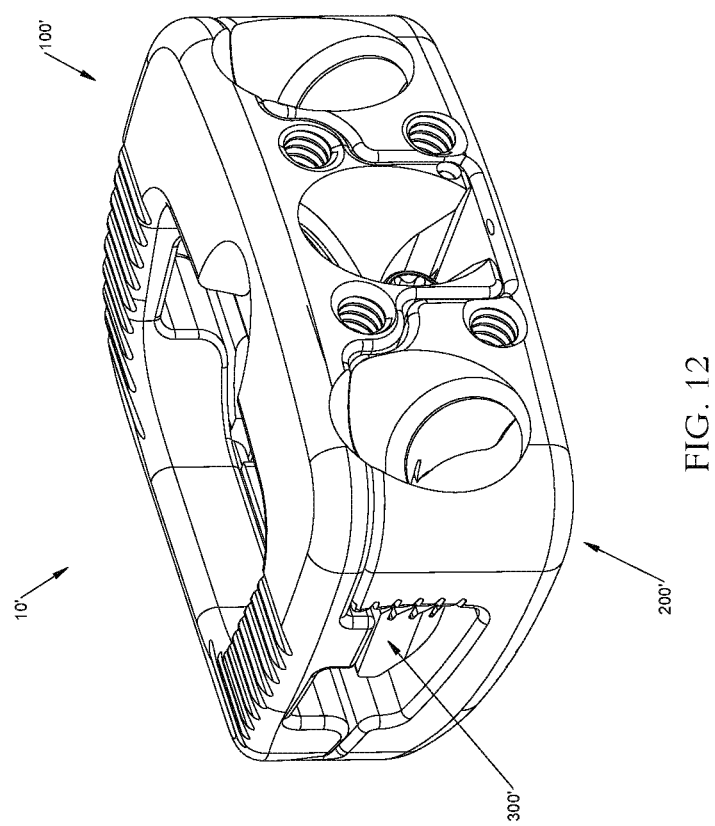
FIG. 12 is a rear, perspective view, of another embodiment of an expandable spinal implant provided in accordance with the present disclosure
Figure 13:
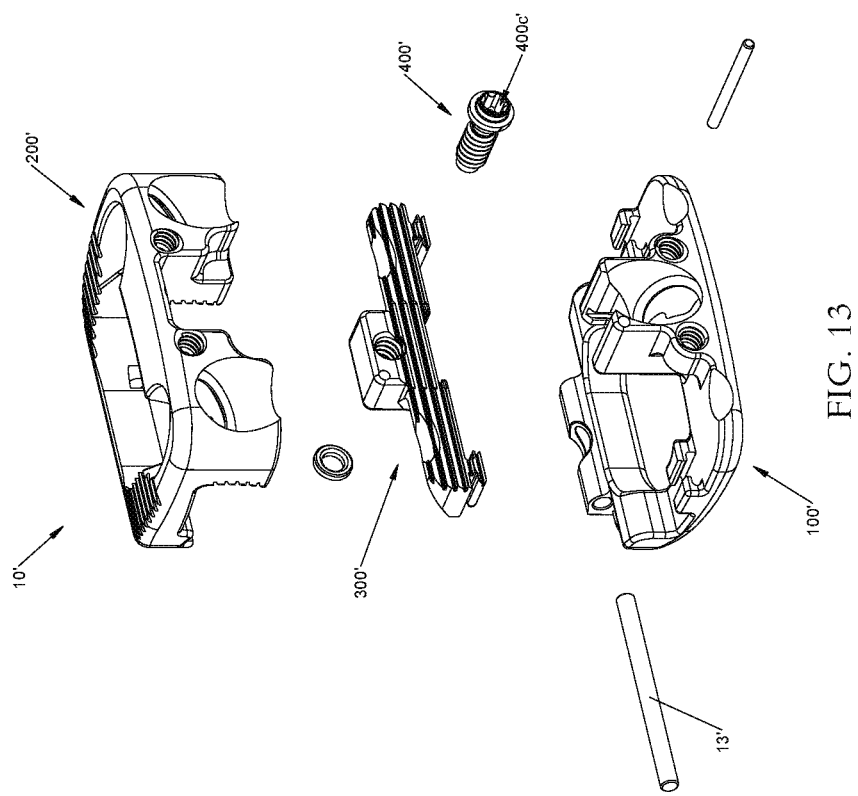
FIG. 13 is an exploded view, with parts separated, of the expandable spinal implant of FIG. 12.
Figure 14:
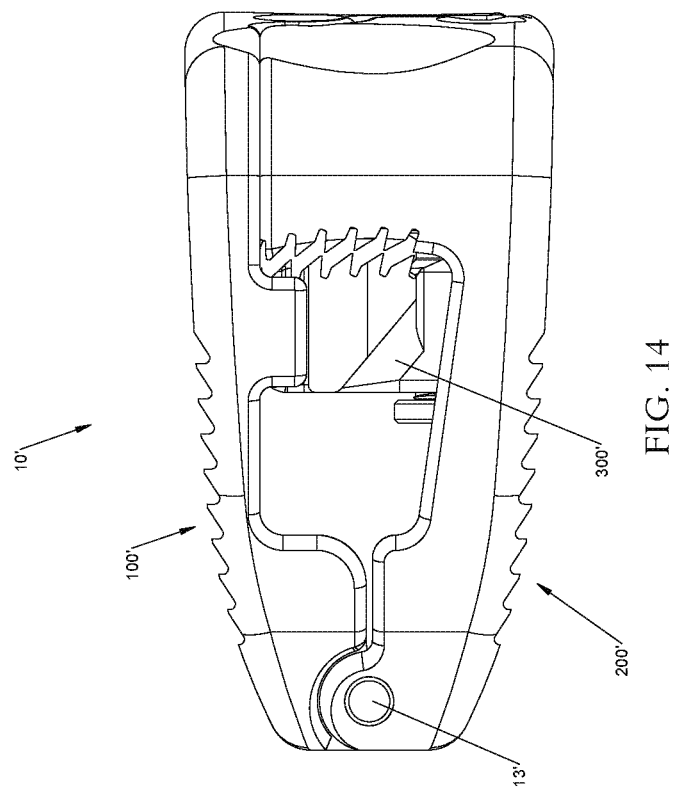
FIG. 14 is a side view of the expandable spinal implant of FIG. 12.

With reference to FIGS. 12-14, in an alternative embodiment, it is contemplated that expandable spinal implant 10' may not include a leaf spring 250 or shuttle nut 310, and rather, ratchet 300' is configured to threadably engage ratchet screw 400'. Specifically, expandable spinal implant 10' includes an upper body 100', a lower body 200', and a ratchet 300' including a ratchet screw 400' (FIG. 13). Upper and lower bodies 100', 200' articulate relative to one another about hinge pin 13' similarly to that described above with respect to expandable spinal implant 10. Ratchet 300' and ratchet screw 400' cooperate to provide a locking mechanism to lock upper and lower bodies 100', 200' in an articulated position relative to each other, thereby maintaining the desired lordosis of the spine. In this manner, ratchet screw 400' threadably engages ratchet 300' such that rotation of ratchet screw 400' causes ratchet 300' to translate between a locked and an unlocked position. Expandable spinal implant 10' is otherwise similar to that of expandable spinal implant 10, and therefore, additional description of expandable spinal implant 10' is not detailed herein in the interest of brevity.

Figure 4B:
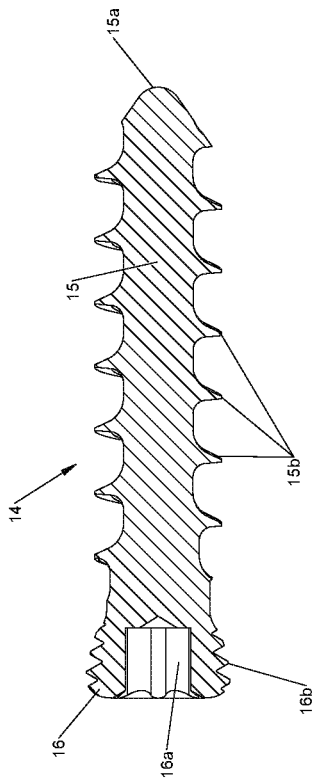
FIG. 4B is a side view of the bone screw of FIG. 4A.
Figure 4C:
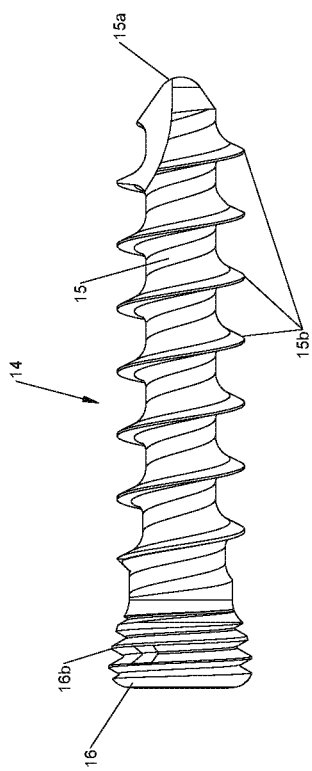
FIG. 4C is a side, cross-sectional view, of the bone screw shown in FIG. 4B.
Figure 4A:
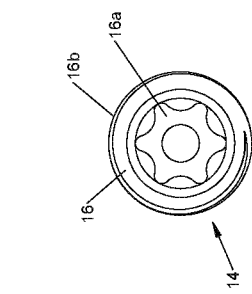
FIG. 4A is a top view of a bone screw usable with the expandable spinal implant of FIG. 1.

Upper and lower bodies 100, 200 are secured to a respective vertebral body by means of bone screws 14 (FIGS. 4A-4C). In this manner, each bone screw 14 substantially retains expandable spinal implant 10 in position relative to the adjacent vertebral bodies. As bone screws 14 are similar to one another, only one is described in detail herein. It is also contemplated that other suitable bone screws 14 be provided for use with expandable spinal implant 10.

Bone screw 14 generally includes a shank 15 and a head 16. Shank 15 defines a distal tip 15a and pitched threading 15b disposed about shank 15. Distal tip 15a and pitched threading 15b facilitate driving bone screw 14 into bone and securement of bone screw 14 therein. Head 16 of bone screw 14 defines a tool-engaging recess 16a. Head 16 further includes a thread 16b for threadably engaging a lip 138b, 238b defined in each one of the plurality of threaded bores 140a, 240, respectively. Pitched threading 15b has a pitch greater than that of thread 16b. Tool-engaging recess 16a may have any shape and/or dimension suitable for transmitting rotational motion from a tool to bone screw 14 (e.g., square, hex, pozidrive, or the like).

For a detailed description of an exemplary expandable spinal implant and exemplary bone screws, reference can be made to U.S. patent application Ser. No. 14/510,598, filed Oct. 9, 2014, and U.S. Patent Application Publication No. 2014/0214166, filed Jan. 25, 2013, the entire contents of each of which are hereby incorporated herein by reference.

Turning now to FIGS. 5-7B, an insertion instrument 500 provided in accordance with the present disclosure is illustrated. Insertion instrument 500 includes an elongate member 502 extending between proximal and distal ends defining longitudinal axis A-A. The proximal end of elongate member 502 includes a handle portion 504 having a circular cross-section. However, it is contemplated that handle portion 504 may include any suitable cross-section capable of facilitating grasping, such as oval, square, rectangular, hexagonal, or the like. Handle portion 504 transitions to an intermediary shaft 506 disposed distal of handle portion 504. Intermediary shaft 506 is co-axial with longitudinal axis A-A and includes a generally cloverleaf shaped cross-section, although it is contemplated that intermediate shaft 506 may be disposed eccentrically relative to longitudinal axis A-A. As can be appreciated, intermediary shaft 506 may include any suitable cross-section, such as circular, oval, square, rectangular, hexagonal, or the like. In embodiments, intermediary shaft 506 is constructed monolithically (i.e., constructed from a single piece of material); however, it is contemplated that intermediary shaft 506 may be constructed from a plurality of elongate tubes that are fixedly secured theretogether using any suitable means, such as welding, adhesive, fasteners, or the like. Although generally described as being formed monolithically with elongate member 502, in certain embodiments, intermediary shaft 506 may be a separate component that is fixedly secured to handle portion 504 using any suitable means, such as those described hereinabove.

Intermediary shaft 506 transitions to an end effector 508 extending distally therefrom, although it is contemplated that end effector 508 may be separately formed from intermediary shaft 506 and fixedly secured thereto using any suitable means, such as those described hereinabove. Although illustrated as including a cross-section similar to that of intermediary shaft 506, it is contemplated that end effector 508 may include any suitable cross-section, such as circular, rectangular, square, oval, hexagonal, or the like. As best illustrated in FIG. 7B, end effector 508 includes a cavity 510 defined on an upper surface 508b thereof configured to receive a shuttle 512 therein as will be described in further detail hereinbelow. Cavity 510 includes a pair of opposed rails 510a disposed on opposed side walls 510b thereof. A worm gear 514 (FIGS. 7A and 10A) is rotatably disposed within cavity 510 and is axially aligned along longitudinal axis A-A. Worm gear 514 includes a length that is generally shorter than that of shuttle 512, although it is contemplated that worm gear 514 may include any suitable length capable of advancing shuttle 512 (i.e., without shearing the teeth off of worm gear 514). A proximal end of the worm gear 514 includes a tool engaging recess 514a defined therein such that a suitable tool can be inserted therein and effectuate rotational motion thereon. Tool engaging recess 514a may be any suitable shape capable of transmitting the rotational motion of the tool to worm gear 514, such as hexalobe, torx, square, pozidrive, or the like. Worm gear 514 may be rotatably retained within cavity 510 using any suitable means known in the art, such as pillow blocks, plates, snap-fit, spindle, or the like. In one non-limiting embodiment, worm gear 514 is retained within cavity 510 by means of a pair of feet (not shown) extending from proximal and distal ends of worm gear 514 retained within corresponding grooves (not shown) defined within cavity 510. Although a distal end surface 508a of end effector 508 is generally shown as including an arcuate profile, it is contemplated that distal end surface 508a may include any suitable shape that corresponds to the shape of the trailing ends 108, 208 of expandable spinal implant 10 such that distal end surface 508a of end effector 508 may sit flush against trailing ends 108, 208 of expandable spinal implant 10.

As best illustrated in FIGS. 7A and 7B, shuttle 512 includes a substantially wedge shaped distal end 512a decreasing in thickness in a distal direction along longitudinal axis A-A, although other suitable profiles are also contemplated, such as concave, convex, or the like. Shuttle 512 includes a pair of opposed slots 516 defined in opposed side surfaces 518 thereof. Each one of the pair of opposed slots 516 is configured to slidably receive a respective one of the pair of rails 510a of cavity 510. In this manner, shuttle 512 is slidably retained within cavity 510 such that shuttle 512 is only permitted to advance or retreat along longitudinal axis A-A (i.e., 2 degrees of freedom), and is prohibited from traveling in any other direction (i.e., pitch, yaw, or roll). A lumen 522 is defined through a proximal end surface 524 of shuttle 512 and extends through a distal end surface 526 thereof. Lumen 522 is configured to receive a suitable tool capable of engaging ratchet screw 400, as will be described in detail hereinbelow. A distal end of shuttle 512 includes a relief 528 defined therein extending proximally along longitudinal axis A-A. Relief 528 removes a lower portion of the wedge shaped distal end 512a and extends proximally therefrom (FIG. 7B). Relief 528 terminates before the midpoint of shuttle 512, such that when shuttle 512 is advanced toward expandable spinal implant 10, the lower portion of the wedge shaped distal end 512a of shuttle 512 does not impact lower body 200 of expandable spinal implant 10. In embodiments, shuttle 512 may not include a relief 528. A plurality of transverse grooves (not shown) are defined in a lower surface (not shown) of shuttle 512 and are configured to threadably engage worm gear 514 such that when worm gear 514 is rotated, shuttle 512 is advanced or retreated within cavity 510 along longitudinal axis A-A.

Additionally, insertion instrument 500 includes a plurality of throughholes defined therethrough (FIGS. 5 and 6). A first throughhole 530 is defined through proximal end surface 502a of elongate member 502 and extends through a proximal end surface 510b of cavity 510. First throughhole 530 is co-axially aligned with worm gear 514 (i.e., along longitudinal axis A-A). First throughhole 530 includes a suitable diameter capable of receiving a suitable tool such that the tool may engage tool engaging recess 514a of worm gear 514, as will be described in further detail hereinbelow. A second and third throughhole 532 and 534 are defined through proximal end surface 502a of elongate member 502 and extend through a distal end surface 508a of end effector 508 (FIG. 7B). Second and third throughholes 532, 534 are arranged spatially about first throughhole 530 such that when insertion instrument 500 is aligned with expandable spinal implant 10, each of second and third throughholes 532, 534 are co-axially aligned with each of the pair of threaded bores 140a of upper body 100. Fourth throughhole 536 is defined through proximal end surface 502a of elongate member 502 and extends through proximal end surface 510c of cavity 510. Fourth throughhole 536 is disposed above first throughhole 530 and is co-axially aligned with lumen 522 of shuttle 512 and ratchet screw 400 of expandable spinal implant 10 such that a suitable tool may be advanced therethrough and engage tool receiving recess 400c of ratchet screw 400 to lock or unlock expandable spinal implant 10, as will be described in further detail hereinbelow.

A pair of screws 540 is disposed in a distal portion of each one of second and third throughholes 532, 534, respectively, and includes a threaded distal portion 542 and a head 544 defined on a proximal portion thereof. Each screw of the pair of screws 540 includes a length such that only a small portion of each screw 540 is disposed within each of second and third throughholes 532, 534 (i.e., mainly the head 544 and a short portion of a shank of the screw 540). In this manner, each screw of the pair of screws 540 only includes a length that is suitable to ensure that insertion instrument 500 remains securely fastened to spinal implant 10. A tool engaging recess 544a is defined within head 544 and is configured to engage a suitable tool as will be described in further detail hereinbelow. Although generally shown as including a hexalobe configuration, tool engaging recess 544a may include any suitable configuration capable of transmitting torque from the tool to screw 540, such as square, pozi, hex, or the like. The screws 540 are configured to be advanced within second and third throughholes 532, 534 such that a distal end (not shown) of head 544 may abut a corresponding boss (not shown) defined on a distal end of second and third throughholes 532, 534. Threaded distal portion 542 is configured to extend distally through second and third throughholes 532, 534 and threadably engage threaded bores 140a of upper body 100.

With reference to FIG. 8A, a first tool suitable for securing insertion instrument 500 to expandable spinal implant 10 is illustrated and generally identified by reference numeral 600. First tool 600 includes an elongate body 602 extending between proximal and distal ends 604 and 606, respectively. Although illustrated as including a circular cross-section, it is contemplated that first tool 600 may include any cross-section suitable for grasping, such as square, hexagonal, or the like. A circumferential groove 608 is defined within an outer surface 602a of elongate body 602 adjacent to proximal end 604 and is configured to enable a suitable handle or driver (not shown) to retain first tool 600 thereon via snap fit or other suitable mechanical means capable of selectively engaging circumferential groove 608. A relief (not shown) or other suitable feature may be defined within outer surface 602a of elongate body to enable rotational motion of the handle to be transferred to first tool 600. Elongate body 602 transitions to a tapered end surface 602b on a distal end 606 thereof which terminates in a distal tip 606a. Distal tip 606a is configured to engage tool engaging recess 544a of each of the pair of screws 540 and tool engaging recess 400c of ratchet screw 400, and therefore, match the configuration of tool engaging recesses 544a, 400c such that rotation of first tool 600 is transferred to the pair of screws 540 and/or ratchet screw 400. In embodiments, distal tip 606a includes a hexalobe configuration.

A second tool suitable for manipulating shuttle 512 along longitudinal axis A-A is illustrated in FIG. 9A and is generally identified by reference numeral 700. Second tool 700 includes an elongate body 702 extending between proximal and distal ends 702a and 702b, respectively, and includes a generally circular cross section; although other cross-sections suitable for grasping are contemplated, such as square, hexagonal, or the like. A circumferential groove 704 is defined within an outer surface 702c of elongate body 702 adjacent proximal end 702a and is configured to enable a suitable handle or driver (not shown) to retain first tool 700 thereon via snap fit or other suitable mechanical means capable of selectively engaging circumferential groove 704. A bulge or protuberance 706 is disposed on outer surface 702c of elongate member 702 distal of circumferential groove 704. Bulge 706 includes a flat annular proximal surface 706a disposed on a proximal end thereof that extends between outer surface 702c of elongate member 702 and an outer surface 706b of bulge 706. A pair of reliefs 706c is defined within flat annular surface 706a and extends distally therefrom. The pair of reliefs 706c extends from outer surface 702c of elongate member 702 to outer surface 706b of bulge 706 and are configured to permit torque to be transferred from a suitable handle or driver to second tool 700. An annular groove 706d is defined within outer surface 706b of bulge 706 distal of the pair of reliefs 706c. Distal of annular groove 706d, outer surface 706b tapers towards outer surface 702c of elongate body 702. Distal end 702b of elongate body 702 defines a distal tip 702d configured to engage tool engaging recess 514a of worm gear 514, and therefore, match the configuration of tool engaging recess 514a of worm gear 514 such that rotation of second tool 700 is transferred to worm gear 514, thereby effectuating movement of shuttle 512 along longitudinal axis A-A. In embodiments, distal tip 702d includes a hexalobe configuration.

With reference to FIGS. 5-11B, the insertion of an expandable spinal implant 10 using insertion instrument 500 is illustrated. Initially, shuttle nut 310 is placed in a first, open position by rotating ratchet screw 400 in a first direction using a suitable tool inserted within tool engaging recess 400c of ratchet screw 400. Alternatively, ratchet 300 may be placed in an intermediate position where leaf spring 250 biases ratchet 300 in a proximal direction such that teeth 302, 232 are in engagement, but are not locked theretogether (i.e., teeth 302, 232 may cam over one another allowing expansion, but preventing collapse). Next, expandable spinal implant 10 is affixed to insertion instrument 500 by threadably engaging the pair of screws 540 with the corresponding plurality of threaded bores 140a of upper body 100. In this manner, each one of the pair of screws 540 is advanced within second and third throughbores 532, 534 of insertion instrument 500. Next, insertion instrument 500 is aligned with expandable spinal implant 10 such that each of the pair of screws 540 is aligned with a corresponding threaded bore of the plurality of threaded bores 140a of upper body 100 (FIGS. 7A and 7B). At this point, first tool 600 is advanced within second throughhole 532 until distal tip 606a engages tool engaging recess 544a of the screw 540, at which time first tool 600 may be rotated to thread the distal threaded portion 542 of the first screw of the pair of screws 540 within the first threaded bore of the plurality of threaded bores 140a of lower body 100 (FIGS. 8A and 8B). The process is repeated for the second screw of the pair of screws 540.

Figures 11A, 11B:
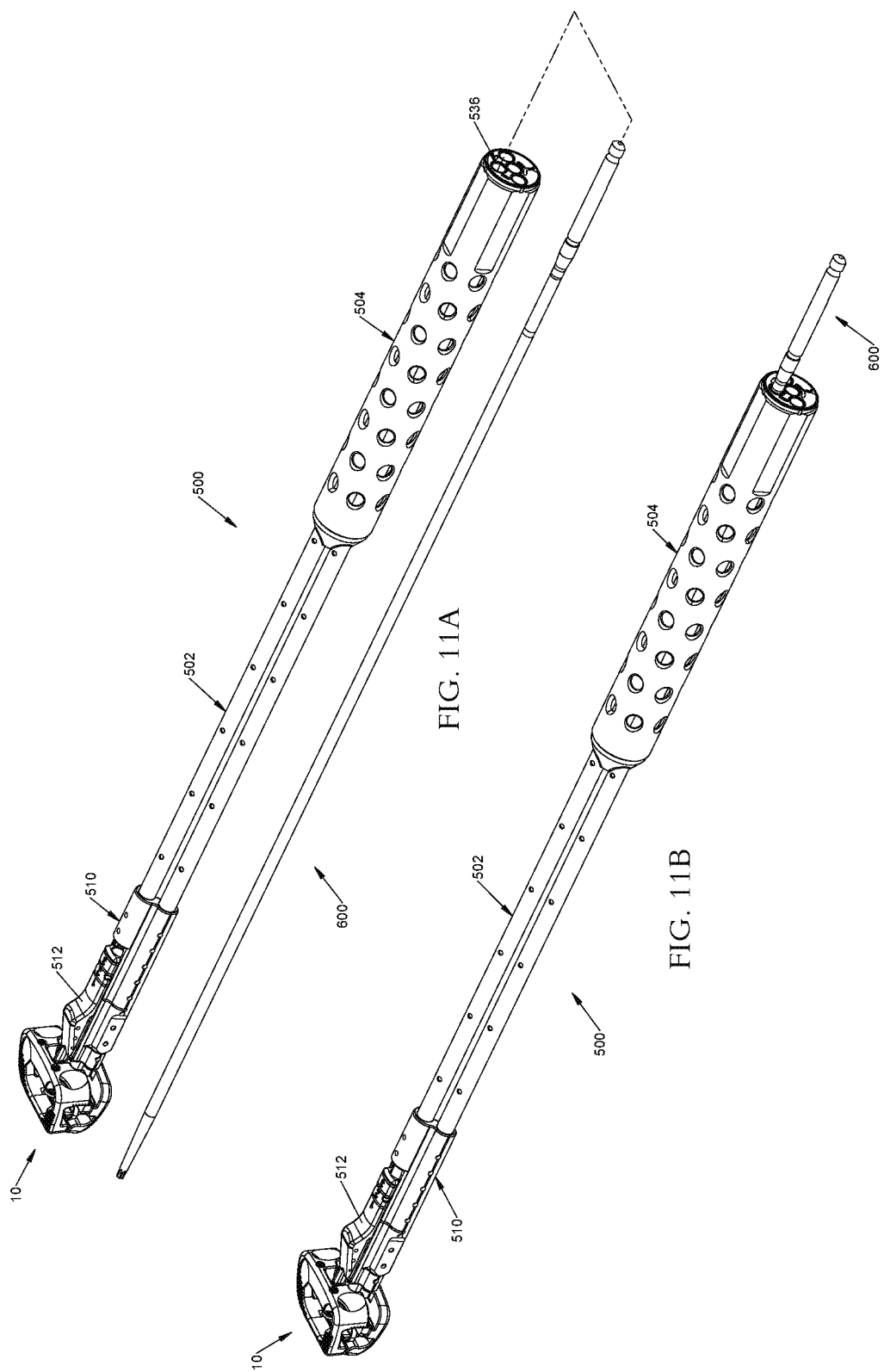
FIG. 11A is a rear, perspective view, of the insertion instrument of FIG. 5, shown with the first tool of FIG. 8A.
FIG. 11B is a rear, perspective view, of the insertion instrument of FIG. 5, shown with the first tool of FIG. 8A disposed within a fourth throughhole defined therein

Next, if shuttle nut 310 of expandable spinal implant 10 was not initially placed in an intermediate position first tool 600 is advanced within fourth throughhole 536 until distal tip 606a engages tool engaging recess 400c of ratchet screw 400, and thereafter rotated such that first tool 600, and thereby ratchet screw 400, are rotated a first direction to place shuttle nut 310 in an intermediate position (FIGS. 11A and 11B). The intervertebral space is then prepared, e.g., damaged or diseased tissue is removed. Thereafter, the cavity defined between openings 100a, 200a of upper and lower bodies 100, 200, respectively, may be packed with bone in-growth material, drugs, or other suitable materials or compounds. Examples of such materials are allograft material, autograft material, calcium phosphate/bone marrow aspirate (BMA), autogenous bone material, or synthetic materials comprised of a biocompatible, osteoconductive, osteoinductive, or osteogeneic material such as VITOSS® Synthetic Cancellous Bone Void Filler material. At this point, expandable spinal implant 10 is advanced within an incision within the patient and thereafter, a previously prepared intervertebral space of the patient's spine. It is contemplated that expandable spinal implant 10 may be advanced within the previously prepared intervertebral space until upper and lower bodies 100, 200 abut a respective vertebral endplate of the patient's spine. Bone screws 14 (FIGS. 4A-4C) are then inserted within screw holes 238 of lower body 200 and are driven into one of the adjacent vertebral bodies. Next, second tool 700 is advanced within first throughhole 530 until distal tip 702d engages tool engaging recess 514a of worm gear 514 (FIGS. 9A and 9B).

Thereafter, second tool 700 may be rotated a first direction to cause expandable spinal implant 10 to articulate about hinge pin 13 to a desired orientation. In this manner, rotation of second tool 700 causes shuttle 512 to be advanced in a distal direction toward expandable spinal implant 10. As second tool 700 is rotated further, shuttle 512 is further advanced distally such that wedge shaped distal end 512a of shuttle 512 contacts lower body 200, thereby causing lower body 200 to articulate about hinge pin 13 relative to upper body 100 as the wedge shaped distal end 512a increases in thickness (FIGS. 10A-10D). This articulation causes teeth 302 and 232 to cam over one another, thereby permitting upper and lower bodies to articulate about hinge pin 13 and increase in height, but not collapse (i.e., expandable spinal implant 10 is partially locked). Articulation of upper body 100 and lower body 200 relative to each other effectuates lordosis of the spine. Alternatively, it is contemplated that upper body 100 and lower body 200 may be articulated relative to each other to effectively fill the intervertebral space without effectuating lordosis of the spine. The desired location of upper body 100 and lower body 200 is selected based on the desired lordosis of the spine. In one exemplary embodiment, teeth 302 and 232, and thereby shuttle 512, are configured to permit the selection of three positions. Once a desired location has been selected, ratchet screw 400 is rotated in the second, opposite direction, using first tool 600, to lock the position of upper body 100 relative to lower body 200 by drawing shuttle nut 310 a proximal direction, thereby drawing teeth 302 of ratchet 300 into engagement with teeth 232 of lower body 200 (FIGS. 11A and 11B). Thereafter, insertion instrument 500 is disengaged from expandable spinal implant 10 using first tool 600 and thereafter, removed from the incision. Once insertion instrument 500 is disengaged from expandable spinal implant 10, a final bone screw 14 is inserted into remaining screw hole 138 of upper body 100 and is driven into the other adjacent vertebral body. Alternatively, each bone screw 14 may be inserted into screw holes 138, 238 of upper and lower bodies 100, 200, respectively after insertion instrument 500 is disengaged from expandable spinal implant 10. Further, it is contemplated that pilot holes be drilled within each respective vertebral body before driving the bone screws 14 therein in order to aid in the driving of bone screws 14 therein.

In some embodiments, the position of upper body 100 relative to lower body 200 may be set prior to inserting expandable spinal implant 10 within the intervertebral space. Once the position of upper body 100 relative to lower body 200 is set, the expandable spinal implant 10 may be advanced into the previously prepared intervertebral space until upper and lower bodies 100, 200 abut a respective vertebral endplate of the patient's spine. Thereafter, the position may continue to be manipulated until the desired lordosis is achieved using the procedure previously described above.

In an alternative embodiment, where ratchet 300' threadably engages ratchet screw 400', ratchet 300' is placed in a first, open position by rotating ratchet screw 400' in a first direction using a suitable tool inserted within tool engaging recess 400c' of ratchet screw 400'. Alternatively, ratchet 300' may be placed in a first, open position, after affixing insertion instrument 500 to expandable spinal implant 10'. Thereafter, the procedure detailed above may be followed. Once the desired lordosis is achieved, ratchet screw 400' may be rotated in the second direction using tool 600 to lock upper body 100' and lower body 200' in the selected position.

The processes detailed above may be repeated as many times as the procedure requires, whether it be for the same expandable spinal implant 10 or for a plurality of expandable spinal implants 10 as required by the procedure being performed.

It will be understood that various modifications may be made to the embodiments of the presently disclosed expandable spinal implant. Therefore, the above description should not be construed as limiting, but merely as exemplifications of embodiments. Those skilled in the art will envision other modifications within the scope and spirit of the present disclosure.

The invention claimed is:

1. An expandable spinal implant, comprising:
a first body and a second body pivotably coupled together for articulation relative to one another between a contracted configuration and an expanded configuration, the first and second bodies being dimensioned to be installed in an intervertebral space between first and second vertebral bodies, and outer surfaces of each of the first and second bodies being adapted to engage an end plate of the respective first and second vertebral bodies, wherein screw holes are defined through the outer surface of the first body and through the outer surface of the second body, and wherein the implant has opposing first and second ends, the first and second bodies being pivotably coupled together at the first end, and the second end having an interface configured for releasable securement to an expansion instrument;
a ratchet mechanism movably coupled to the first body and configured to engage the second body, the ratchet mechanism being biased into engagement with the second body such that the first and second bodies are capable of articulating relative to each other in a first direction, but are prevented from articulating relative to each other in a second direction; and
a plurality of bone screws, each bone screw of the plurality of bone screws insertable through a corresponding screw hole of the first and second bodies, wherein the plurality of bone screws are capable of being attached to bone.

2. The implant of claim 1, wherein each of the screw holes defined through the outer surfaces of the first and second bodies communicate with a respective bore extending at an oblique angle through an adjacent side surface of the respective first and second body.

3. The implant of claim 1, wherein the ratchet mechanism is disposed at the second end.

4. The implant of claim 1, wherein the ratchet mechanism is biased into engagement with the second body by a spring.

5. The implant of claim 4, wherein the spring is shaped to at least partially surround an open region.

6. The implant of claim 5, wherein the open region communicates with and is aligned between an opening through the first body and an opening through the second body.

7. The implant of claim 1, wherein the ratchet mechanism is transitionable between an engaged state, a disengaged state, and a locked state; wherein, in the engaged state, the ratchet mechanism permits the first and second bodies to articulate relative to one another in the first direction while preventing the first and second bodies from articulating relative to one another in the second direction, the first direction being towards the expanded configuration and the second direction being towards the contracted configuration; wherein, in the locked state, the ratchet mechanism prevents the first and second bodies from articulating relative to one another in both the first direction and the second direction; and wherein, in the disengaged state, the ratchet mechanism does not prevent the first and second bodies from articulating relative to one another in either the first direction or the second direction.

8. The implant of claim 7, wherein the ratchet mechanism is transitionable between the engaged state, the disengaged state, and the locked state by rotation of a screw.

9. The implant of claim 7, wherein the ratchet mechanism is transitionable between the engaged state, the disengaged state, and the locked state by translation of a shuttle within a cavity in the ratchet mechanism.

10. An expandable spinal implant, comprising:
a first body and a second body pivotably coupled together for articulation relative to one another between a contracted configuration and an expanded configuration, the first and second bodies being dimensioned to be installed in an intervertebral space between first and second vertebral bodies, and outer surfaces of each of the first and second bodies being adapted to engage an end plate of the respective first and second vertebral bodies; and
a ratchet mechanism slidably coupled to the first body, the ratchet mechanism including a plurality of teeth engageable with a plurality of teeth on the second body, the ratchet mechanism being slidably coupled to the first body such that the ratchet mechanism is linearly translatable relative to the first body to move the teeth of the ratchet mechanism into and out of engagement with the teeth of the second body, the ratchet mechanism being biased into engagement with the teeth of the second body such that the first and second bodies are capable of articulating relative to each other in a first direction, but are prevented from articulating relative to each other in a second direction.

11. The implant of claim 10, wherein the implant has opposing first and second ends, the first and second bodies being pivotably coupled together at the first end, and the second end having an interface configured for releasable securement to an expansion instrument.

12. The implant of claim 10, wherein the implant has opposing first and second ends, the first and second bodies being pivotably coupled together at the first end, and the ratchet mechanism being disposed at the second end.

13. The implant of claim 10, wherein the ratchet mechanism is biased into engagement with the second body by a spring.

14. The implant of claim 13, wherein the spring is shaped to at least partially surround an open region.

15. The implant of claim 14, wherein the open region communicates with and is aligned between an opening through the first body and an opening through the second body.

16. The implant of claim 10, wherein the ratchet mechanism is transitionable between an engaged state, a disengaged state, and a locked state; wherein, in the engaged state, the ratchet mechanism permits the first and second bodies to articulate relative to one another in the first direction while preventing the first and second bodies from articulating relative to one another in the second direction, the first direction being towards the expanded configuration and the second direction being towards the contracted configuration; wherein, in the locked state, the ratchet mechanism prevents the first and second bodies from articulating relative to one another in both the first direction and the second direction; and wherein, in the disengaged state, the ratchet mechanism does not prevent the first and second bodies from articulating relative to one another in either the first direction or the second direction.

17. The implant of claim 16, wherein the ratchet mechanism is transitionable between the engaged state, the disengaged state, and the locked state by rotation of a screw.

18. The implant of claim 16, wherein the ratchet mechanism is transitionable between the engaged state, the disengaged state, and the locked state by translation of a shuttle within a cavity in the ratchet mechanism.

19. The implant of claim 18, wherein the cavity is defined between a first internal wall and a second internal wall; wherein the shuttle is transitionable between a first position and a second position, the shuttle being in contact with the first internal wall in the first position and the shuttle being in contact with the second internal wall in the second position; and wherein the shuttle is in the first position when the ratchet mechanism is in the locked state, and the shuttle is in the second position when the ratchet mechanism is in the disengaged state, the shuttle being positioned in an intermediate position spaced apart from the first internal wall and the second internal wall when the ratchet mechanism is in the engaged state.

* * * * *